United States Patent
Zheng et al.

(10) Patent No.: US 9,480,411 B2
(45) Date of Patent: Nov. 1, 2016

(54) ELECTROCARDIOGRAM BASELINE REMOVAL

(75) Inventors: Ling Zheng, Andover, MA (US); Yu Chen, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 313 days.

(21) Appl. No.: 14/343,359

(22) PCT Filed: Jun. 7, 2012

(86) PCT No.: PCT/US2012/041386
§ 371 (c)(1),
(2), (4) Date: Mar. 6, 2014

(87) PCT Pub. No.: WO2013/036307
PCT Pub. Date: Mar. 14, 2014

(65) Prior Publication Data
US 2014/0222350 A1    Aug. 7, 2014

Related U.S. Application Data (60) Provisional application No. 61/532,327, filed on Sep. 8, 2011.

(51) Int. Cl.
*A61B 5/04* (2006.01)
*A61B 5/00* (2006.01)
*G06K 9/00* (2006.01)

(52) U.S. Cl.
CPC ......... *A61B 5/04017* (2013.01); *A61B 5/7203* (2013.01); *A61B 5/725* (2013.01); *G06K 9/00503* (2013.01)

(58) Field of Classification Search
CPC  A61B 5/04017; A61B 5/725; A61B 5/7203; G06K 9/0053
See application file for complete search history.

(56) References Cited

U.S. PATENT DOCUMENTS

| | | | |
|---|---|---|---|
| 5,762,068 A * | 6/1998 | dePinto | H03H 17/04 |
| | | | 128/901 |
| 5,913,308 A | 6/1999 | Forbes et al. | |
| 2002/0025017 A1 | 2/2002 | Stergiopoulos et al. | |
| 2003/0028349 A1 | 2/2003 | Gross et al. | |
| 2009/0234239 A1 | 9/2009 | Shani et al. | |
| 2011/0066042 A1 | 3/2011 | Pandia et al. | |

FOREIGN PATENT DOCUMENTS

| | | |
|---|---|---|
| WO | WO-2008038220 A1 | 4/2008 |
| WO | WO-2010054409 A1 | 5/2010 |

OTHER PUBLICATIONS

Karagiannis et al: "Noise-Assisted Data Processing With Epirical Mode Decomposition in Biomedical Signals", IEEE Transactions on Information Technology in Biomedicine, IEEE Service Center, Los Alamitos, CA, US, vol. 15, No. 1, Jan. 1, 2011, pp. 11-18.
International Search Report and Writtin Opinoiin issued in PCT/US2012/041386 on Aug. 29, 2012.

* cited by examiner

*Primary Examiner* — Mallika D Fairchild
(74) *Attorney, Agent, or Firm* — Jones Day (57) ABSTRACT

A system includes a low pass-filter and a Savitzky-Golay filter. The low-pass filter receives and processes a first electrocardiogram signal. The filter removes at least the high frequency components of the first electrocardiogram signal. The Savitzky-Golay filter estimates a baseline variation of the first electrocardiogram signal from the filtered first electrocardiogram signal. Related apparatus, systems, techniques and articles are also described.

17 Claims, 8 Drawing Sheets

ELECTROCARDIOGRAM BASELINE REMOVAL

CROSS REFERENCE TO RELATED APPLICATION

This application is a national phase entry of International Application No. PCT/US2012/041386, filed Jun. 7, 2012, which claims the benefit of the filing date of U.S. Provisional Application No. 61/532,327, filed on Sep. 8, 2011, the contents of each are herein incorporated by reference.

TECHNICAL FIELD

The subject matter described herein relates to techniques, methods, systems and articles for removing low frequency signal components from physiological signals such as electrocardiogram signals.

BACKGROUND

Figure 1:
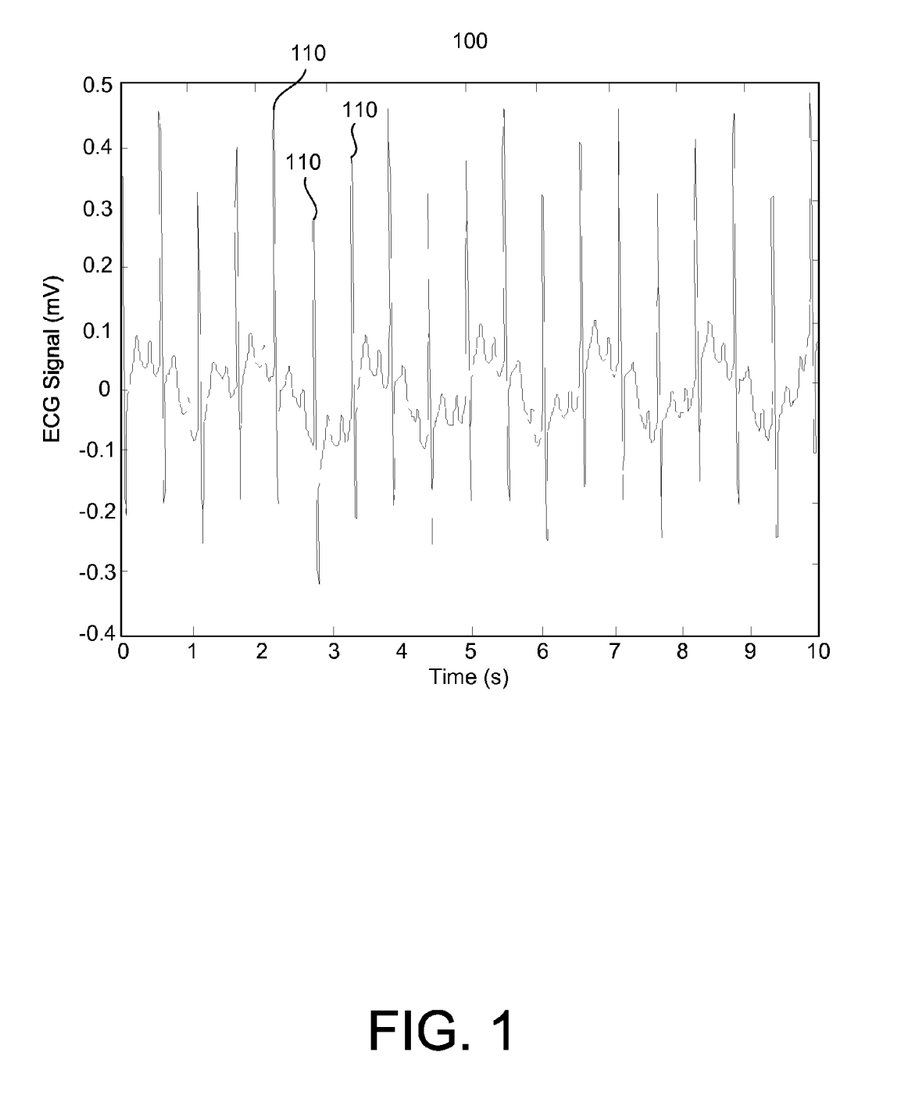
FIG. 1 is a plot showing an example ECG signal containing baseline variation.

An electrocardiogram (ECG) is a test that records the electrical activity of the heart as recorded by electrodes attached to the outer surface of the skin. Impedance variation between the recording electrode and the skin due to respiration or other body movement can cause baseline variations (also referred to as low frequency wander) in the ECG signal. Baseline variation is one type of noise in electrocardiogram signals. FIG. 1 is a plot 100 showing an example ECG signal containing baseline variation. QRS complexes 110 can be identified by sharp spikes in the signal.

There are a variety of methods for baseline removal from the ECG, including high-pass filtering, adaptive filtering, wavelet transform, time-frequency analysis, curve fitting, etc. One approach, which is a special type of curve fitting, is the cubic spline method. A cubic spline is fitted on isoelectric reference points to estimate the baseline. The cubic spline method can be prone to error in the calculation of the isoelectric reference points, especially in the presence of noise.

ECG baseline variation can comprise a low frequency signal within a range of 0 to 0.8 Hz. According to the American Health Association (AHA), the frequency in the ECG signal is typically above 0.05 Hz. Since the frequency band of the baseline noise overlaps with the ECG signal of interest, a simple high-pass filter is not sufficient for removing the baseline.

Another approach to baseline removal is to use a high-pass filter. However, since the baseline is a type of in-band noise, a cut-off frequency cannot be set that would completely separate the ECG signal from the baseline. An approach adapting the cutoff frequency of the baseline filter to the heart rate was introduced by L. Lundstrom in 1995. According to Fourier theory, the frequency spectrum of a periodic signal is non-zero only on the base frequency and harmonics. This means that if the period is T, the lowest frequency is 1/T. An ideal ECG, which has constant heart rate and identical morphology for each heart beat, can be treated as a periodic signal, such that the lowest frequency is HeartRate/60 (Hz). If the cutoff frequency is set to this value, the low frequency noise can be removed. However, when the heart rate is low, this approach can not remove the baseline variation completely.

SUMMARY

In one aspect, a system includes a low pass-filter and a Savitzky-Golay filter. The low-pass filter receives and processes a first electrocardiogram signal. The filter removes at least the high frequency components of the first electrocardiogram signal. The Savitzky-Golay filter estimates a baseline variation of the first electrocardiogram signal from the filtered first electrocardiogram signal.

In another aspect, a first electrocardiogram signal is received. The first electrocardiogram signal is processed in a filter to remove at least high frequency components of the first electrocardiogram signal. The filtered first electrocardiogram signal is processed in a Savitzky-Golay filter to estimate a baseline variation of the first electrocardiogram signal. The estimate of the baseline variation is provided.

One or more of the following features can be included. For example, a delay module and a combination module can be included. The delay module can time shift the first electrocardiogram signal and the combination module can combine the time shifted first electrocardiogram signal and the baseline variation estimate to produce a second electrocardiogram signal with the baseline variation removed. A down-sampler and an up-sampler can be included. The down-sampler can reduce the sampling rate of the filtered first electrocardiogram signal and the up-sampler can increase the sampling rate of the baseline variation estimate.

The low-pass filter can have a cutoff frequency of about 0.8 hertz. The first electrocardiogram signal can be sampled at a rate of about 500 hertz. The polynomial order or degree can be 2 or greater. The polynomial degree of the Savitzky-Golay filter can be between about 2 and about 10. The window size of the Savitzky-Golay filter can be less than about 750. The down-sampler can reduce the sample rate of the filtered first electrocardiogram signal by a factor of about 40 and the up-sampler can increase the sample rate of the baseline variation estimate by a factor of about 40. The up-sampler can perform linear interpolation. Providing the estimate of the baseline variation can include providing for further processing, storage, transmission, or display.

Articles of manufacture are also described that comprise computer executable instructions permanently stored (e.g., non-transitorily stored, etc.) on computer readable media, which, when executed by a computer, causes the computer to perform operations herein. Similarly, computer systems are also described that may include a processor and a memory coupled to the processor. The memory may temporarily or permanently store one or more programs that cause the processor to perform one or more of the operations described herein. In addition, methods can be implemented by one or more data processors either within a single computing system or distributed among two or more computing systems.

The subject matter described herein provides many advantages. For example, knowledge of heart rate is not required to perform baseline variation removal. Additionally, distortion can be reduced by using filters with linear phase and the baseline variation can be completely removed even when there is spectral overlap between the baseline and the ECG signal. Further, information about the isoelectric points of the ECG signal may not be required and the delay introduced by processing can be minimal. The current subject matter can be insensitive to noise, easier to implement and suited to implementation on ECG monitoring systems.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 2:
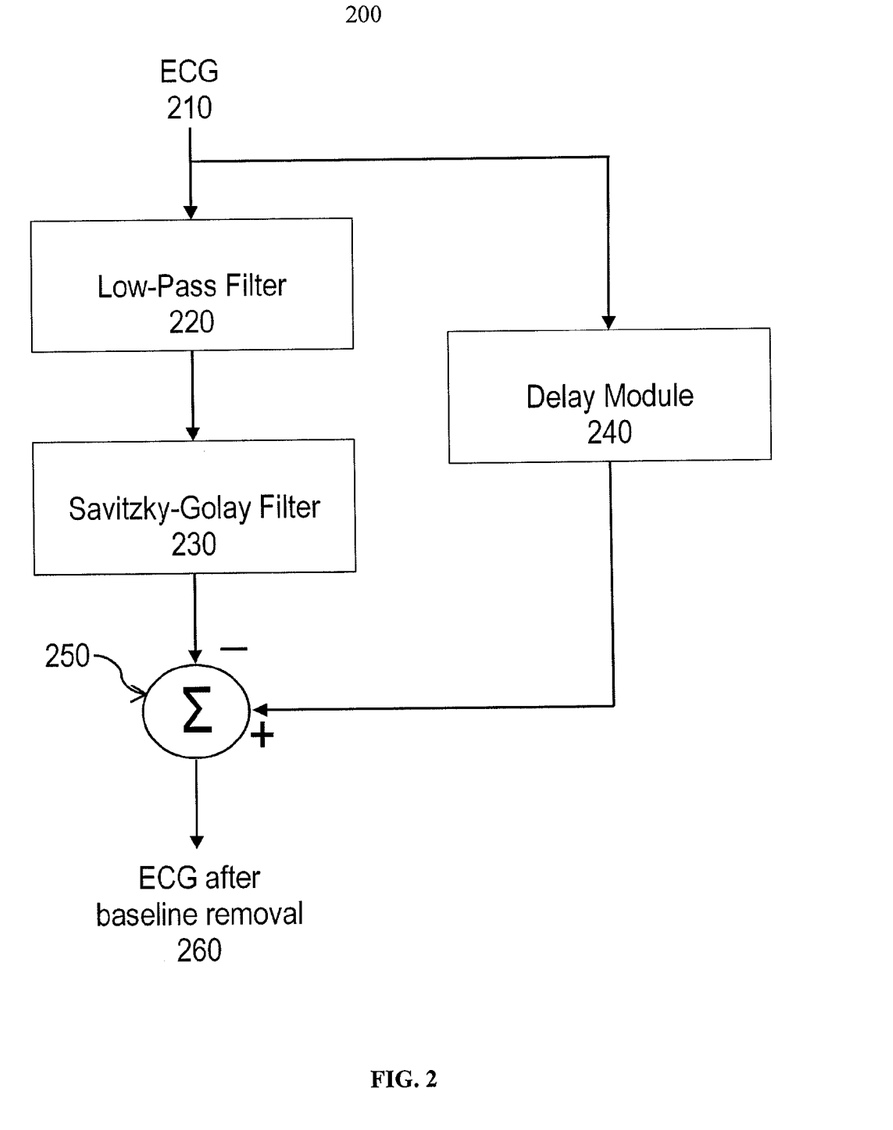
FIG. 2 is a system diagram of an ECG baseline variation removal system.

FIG. 2 is a system diagram 200 of an ECG baseline variation removal system. An input ECG 210 is passed to a low-pass filter 220 to produce a filtered signal which has the high frequency components of the signal removed. The filtered signal is then passed to a Savitzky-Golay (SG) filter 230 which creates an estimate of the baseline variation of the input ECG 210. The SG filter is a filter that performs a local polynomial regression (of degree k) on a series of values (of at least k+1 points) to determine a smoothed value for each point. One advantage of this approach is that it preserves features of the distribution such as relative maxima, minima and width, which are usually 'flattened' by other adjacent averaging techniques (like moving averages, for example). The ECG 210 can also be passed to a delay module 240 to be delayed in time (e.g., time shifted). The delay can compensate for any delays introduced by the low-pass filter 220 and SG filter 230 processing so that the input ECG 210 can, in a combination module 250, be combined with the estimated baseline variation produced by the SG filter 230 to produce an output ECG with the baseline variation removed 260.

The low-pass filter can be, for example, a symmetric finite impulse response (FIR) filter with 100 taps and a cutoff frequency of 0.8 Hz. The low-pass FIR filter can remove the sharp QRS spikes (e.g., label 110 in FIG. 1) to improve the estimation of the baseline by the SG filter. The properties of the SG filter are determined by a window length and polynomial order or degree. The polynomial order or degree can be 2 or greater. For example, the polynomial order or degree can be specified to be between about 2 and about 10 and when the input ECG is sampled at 500 Hertz, the window size can be about 750 samples or less. The window size can depend on the input ECG sample rate and be adjusted accordingly. The longer the window and the lower the polynomial order, the lower the cutoff frequency. For example, if the ECG signal is sampled at 500 Hz, a window size of 2*250+1 and a polynomial order of 2 is specified, then the SG filter will introduce about 500 milliseconds of delay and the computational load will be equivalent to a FIR filter with 650 taps.

Figure 5:
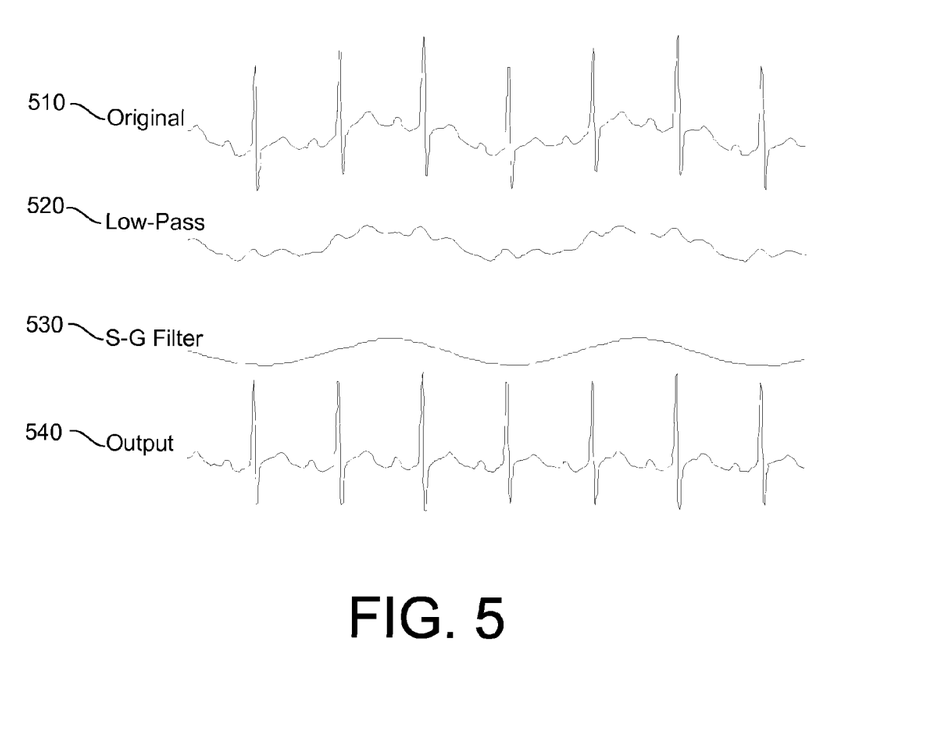
FIG. 5 is a plot illustrating an example ECG, and signals measured from the output of different components of a system in accordance with the current subject matter.

Referring now to FIG. 5 with further reference to FIG. 2. FIG. 5 is a plot illustrating an example input ECG 510, a corresponding filtered signal 520 generated by the low-pass filter 220, a corresponding baseline variation 530 generated by the SG filter 230, and an output ECG 540 produced by the combination module 250. The duration of each signal shown is four seconds, and the average R-wave peak amplitude is 0.9 mV. The example input ECG was collected from a patient and the baseline variation caused by respiration is evident. The QRS complexes have been removed from the filtered signal 520; however P and Q waves have not been removed. The baseline variation estimate 530 is a smooth signal that approximates the baseline variation evident in the example ECG input 510. The output ECG 540 is the example input ECG 510 with the baseline variation estimate 530 removed.

Figure 6:
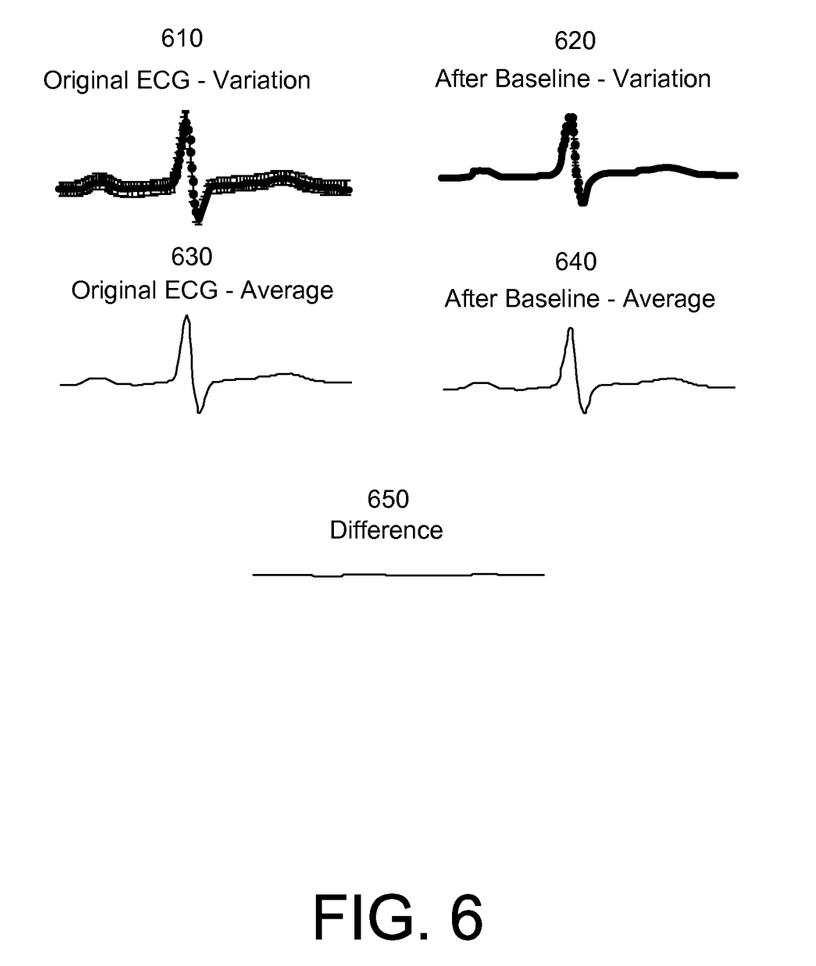
FIG. 6 is a plot showing a comparison of an input ECG and an output ECG of a system in accordance with the current subject matter.

FIG. 6 is a plot showing forty-nine beats of the example input ECG 510 and output ECG 540 that have been divided into one-heart-beat segments and time shifted to align their R-wave peaks. At 610, each segment of the example ECG has been superimposed and a high variation between heart beat segments is evident. At 620, each segment of the output signal has been superimposed and a low variation between heart beat segments is evident. At 630 and 640, the average of the segments is shown for the example input ECG and output ECG respectively. Since the baseline variation noise is not synchronized to the heart rate, the average of the example input ECG segments can be considered baseline free (i.e., the variation averages to zero). At 650, the difference between 630 and 640 is shown. The difference is close or almost zero (i.e. a straight line), showing that the baseline variation has been successfully removed.

Figure 7:
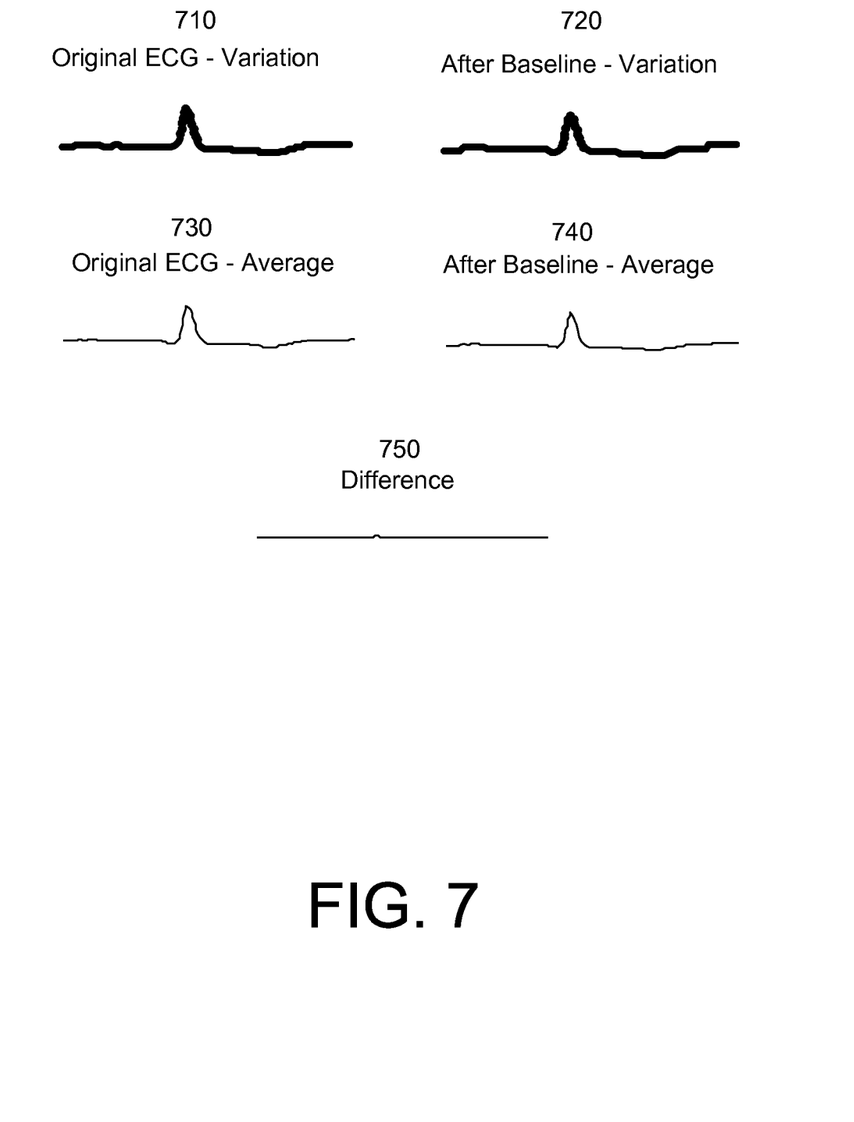
FIG. 7 is a plot illustrating the limited distortion introduced by the current subject matter.

FIG. 7 is a plot illustrating the limited distortion introduced by the current subject matter. To further characterize performance, an ECG without any baseline variation is used as input. FIG. 7 shows an ECG without baseline variation and the ECG after baseline variation removal. Both have been divided into multiple one-heart-beat segments and time shifted to align their R-wave peaks. At 710 each segment of the input ECG is superimposed and 730 shows their average. At 720, each segment of the output ECG is superimposed and 740 shows their average. 750 is the difference between 730 and 740. The difference is near zero and therefore indicates that the distortion provided by the current subject matter is minimal.

Figure 8:
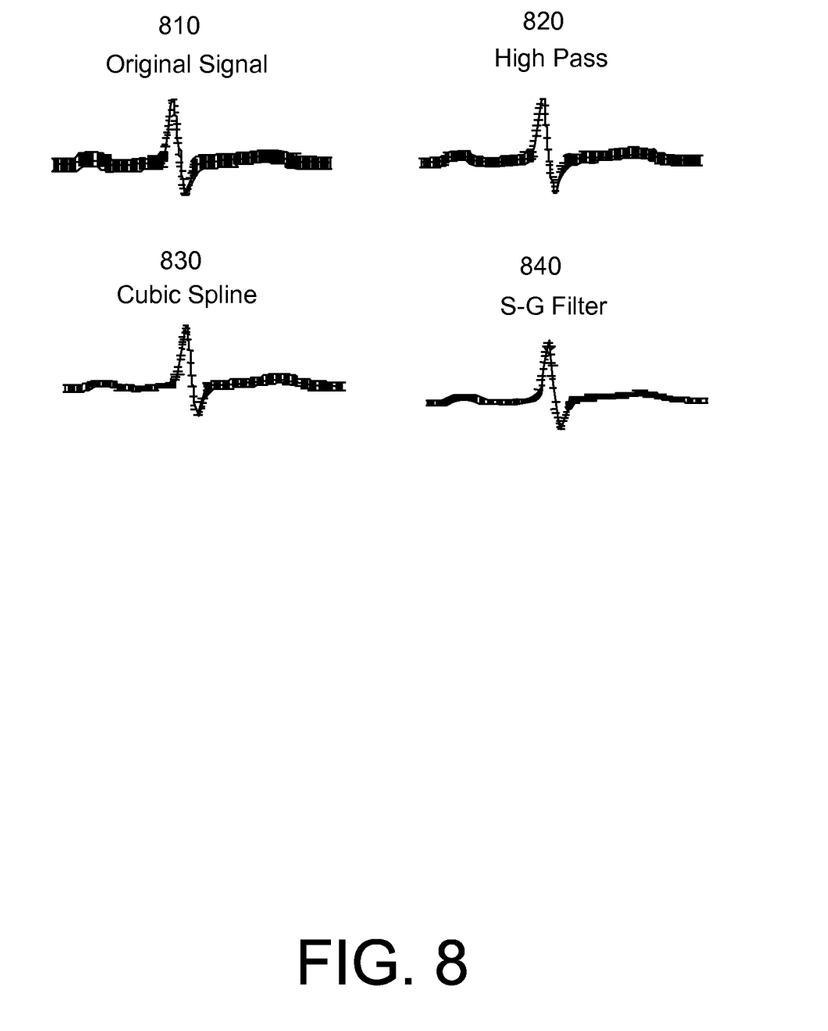
FIG. 8 is a plot showing a performance comparison between the current subject matter, a high-pass filter method and a cubic spline method.

FIG. 8 is a plot comparing the performance between the current subject matter, a high-pass filter method and a cubic spline method. An input ECG containing baseline variation which has been divided into one-heart-beat segments and time shifted to align their R-wave peaks and superimposed is presented at 810. A similar presentation is provided for ECGs that have been processed by a high-pass method 820, a cubic spline 830, and the current subject matter 840. It is evident from FIG. 8 that 840 presents an output ECG with the least variability and therefore is an improvement over the high-pass method, cubic spline method, or no processing at all. Additional tests were performed using an input ECG containing motion artifacts and an artificial 0.8 Hz sinusoid and similar results were found.

Figure 3:
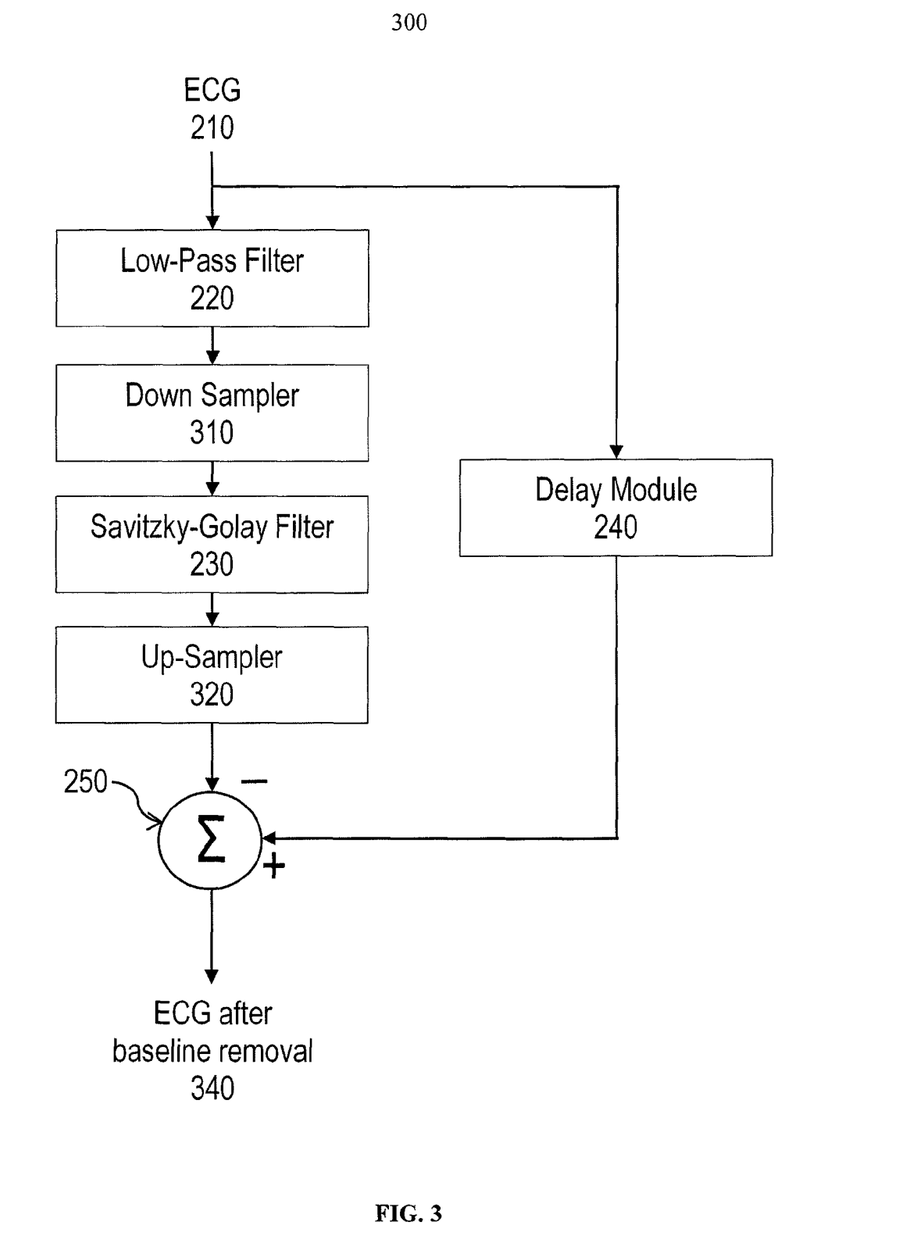
FIG. 3 is a system diagram of an ECG baseline variation removal system with down and up samplers.

FIG. 3 is a system diagram 300 of an ECG baseline variation removal system. The input ECG 210 is passed to an anti-aliasing low-pass filter 220. The anti-aliasing filter low-pass filter can be an infinite impulse response (IIR)

filter. The filtered ECG is down-sampled by down-sampler 310 and passed to SG filter 330. The SG filter creates an estimate of the baseline variation of the input ECG 210. The estimate is up-sampled by up-sampler 320. The up-sampling can be, for example, a linear interpolation. The ECG signal 210 can also be delayed by delay module 240. The delay can compensate for any delays introduced by the anti-aliasing low-pass filter 220, down-sampler 310, SG filter 230, and up-sampler 320 processing so that the input ECG 210 can, in combination module 250, be combined with the estimated baseline variation produced by the SG filter 230 to produce an output ECG with the baseline variation removed 340.

If the input ECG 210 has a sampling rate of 500 Hz, is down-sampled by a factor of 40 to a 12.5 Hz rate, and assuming the SG filter window size is 2*6+1 and the polynomial order is 2, then the delay will be 540 milliseconds and the computational load will be equivalent to a FIR filter with 17 taps. The baseline variation estimate can be up-sampled by a factor of 40 to combine the input ECG.

Figure 9:
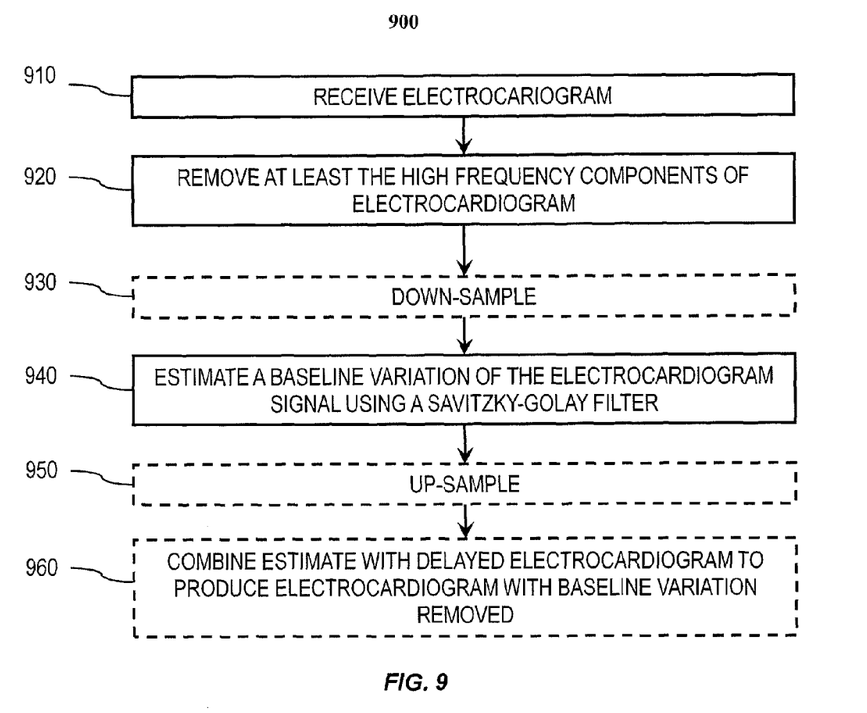
FIG. 9 is a process flow diagram illustrating a method a removing baseline variation from an ECG.

FIG. 9 is a process flow diagram 900 illustrating a method a removing baseline variation from an ECG. At 910, the ECG is received. The ECG can have a sample rate of about 500 Hz. At 920, at least the high frequency components of the ECG are removed. The high frequency components can be frequencies above about 0.8 Hz. Optionally, at 930, the processed ECG can be down-sampled. At 940, a baseline variation of the ECG can be estimated using a SG filter. The window length and polynomial degree of the SG filter can be selected based on the sample rate and baseline variation frequency. Optionally, at 950, the estimate can be up-sampled. Optionally, at 960, the estimate can be combined with a delayed ECG to produce an ECG with the baseline variation removed. Additionally, the baseline variation estimate can be provided for further processing, transmission, storage or display.

The SG filter determines a smoothed value for each data point in a series by performing a local polynomial fit in a window of predetermined length. The polynomial function can be defined as:

$$p(n) = a_0 n^0 + a_1 n^1 + a_2 n^2 + \ldots + a_M n^M$$

Figure 4:
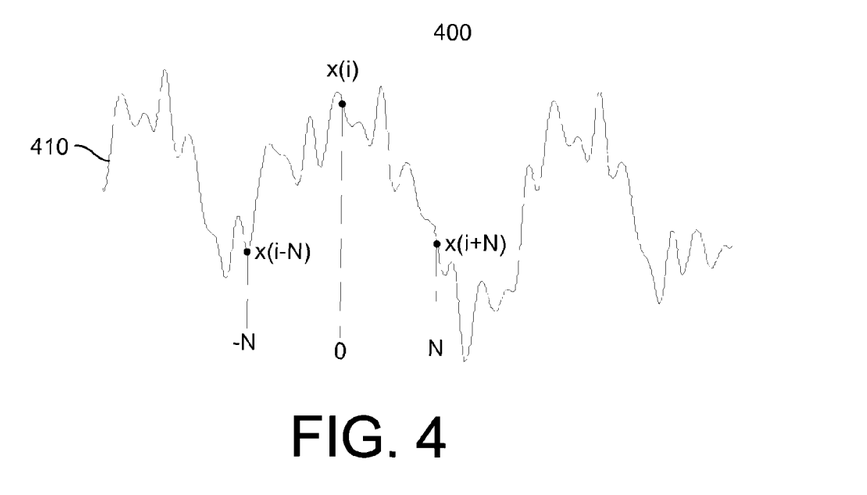
FIG. 4 is a plot of a time series illustrating a window used for a Savitzky-Golay polynomial fit.

M is the polynomial order, n is a independent variable, and $a_0, a_1, \ldots, a_M$ are polynomial coefficients. FIG. 4 is a plot 400 of a time series 410. x(i) represents the time series 410 at any arbitrary sample i. The window length can be 2*N+1, and then a least squares polynomial fit centered at the ith sample can be expressed as a matrix equation BA=X, namely, $$\begin{bmatrix} (-N)^0 & (-N)^1 & \ldots & (-N)^M \\ \vdots & \vdots & \vdots & \vdots \\ (-1)^0 & (-1)^1 & \ldots & (-1)^M \\ (0)^0 & 0 & 0 & 0 \\ (1)^0 & 1 & \ldots & 1^M \\ \vdots & \vdots & \vdots & \vdots \\ (N)^0 & N^1 & \ldots & N^M \end{bmatrix} \begin{bmatrix} a_0 \\ a_1 \\ \vdots \\ a_M \end{bmatrix} = \begin{bmatrix} x(i-N) \\ \vdots \\ x(i-1) \\ x(i) \\ x(i+1) \\ \vdots \\ x(i+N) \end{bmatrix}.$$

A least-squares solution can be expressed as $A = (B^T B)^{-1} B^T X$ and the smoothed value of the ith sample, denoted as y(i), can then be calculated as $$y(i) = a_0 n^0 + a_1 n^1 + a_2 n^2 + \ldots + a_M n^M |_{n=0} = a_0.$$

From the above-mentioned equation, the smoothed value is determined by $a_0$ only. $a_0$ is the inner product between the first row in $(B^T B)^{-1} B^T$ and X. The matrix B is determined by the window size, 2*N+1, and the polynomial order, M. Therefore, $(B^T B)^{-1} B^T$ can be known once the window size and the polynomial order are known. Let the first row in $(B^T B)^{-1} B^T$ be [h(-N) ... h(-1) h(0) h(1) ... h(N)], then y(i) can be written as $$y(i) = \sum_{n=-N}^{n=N} h(n) x(i+n).$$

As the first row in $(B^T B)^{-1} B^T$ is symmetric with respect to the central point, n=0, y(i) can be written as $$y(i) = \sum_{n=-N}^{n=N} h(n) x(i-n).$$

The right hand side of the above equation is the convolution between h(n) and x(n). Therefore, the output of the SG filter can be expressed as the input filtered by a FIR filter that is determined by the window size and the polynomial order. Further, the SG filter has a linear phase response and a delay of half the window size.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:
1. A system comprising:
a low-pass filter configured to receive and process a first electrocardiogram signal, the low-pass filter removing at least high frequency components of the first electrocardiogram signal thereby producing a filtered first electrocardiogram signal;

a down-sampler configured to reduce a sampling rate of the filtered first electrocardiogram signal;

a Savitzky-Golay filter configured to estimate a baseline variation of the first electrocardiogram signal from the down-sampled filtered first electrocardiogram signal;

an up-sampler configured to increase a sampling rate of the baseline variation;

a delay module configured to time shift the first electrocardiogram signal thereby producing a time shifted first electrocardiogram signal; and a combination module configured to combine the time shifted first electrocardiogram signal and the up-sampled baseline variation thereby producing a second electrocardiogram signal with the baseline variation removed;

wherein the second electrocardiogram signal is provided by at least one of displaying the second electrocardiogram signal in an electronic visual display, transmitting the second electrocardiogram signal to a remote computing system, storing the second electrocardiogram signal in a physical storage media, or loading the second electrocardiogram signal into memory.

2. The system of claim 1, where the low-pass filter has a cutoff frequency of 0.8 hertz.

3. The system of claim 1, wherein the first electrocardiogram signal is sampled at a rate of 500 hertz.

4. The system of claim 1, wherein a polynomial degree of the Savitzky-Golay filter is between 2 and 10.

5. The system of claim 1, wherein a window size of the Savitzky-Golay filter is less than 750.

6. The system of claim 1, wherein the down-sampler reduces the sample rate of the filtered first electrocardiogram signal by a factor of 40 and the up-sampler increases the sample rate of the baseline variation by a factor of 40.

7. The system of claim 1, wherein the up-sampler performs linear interpolation.

8. A method comprising:
receiving a first electrocardiogram signal;
processing the first electrocardiogram signal in a filter thereby removing at least high frequency components of the first electrocardiogram signal, producing a filtered first electrocardiogram signal;
down-sampling the filtered first electrocardiogram signal;
processing the down-sampled filtered first electrocardiogram signal in a Savitzky-Golay filter to estimate a baseline variation of the first electrocardiogram signal;
up-sampling the baseline variation;
delaying the first electrocardiogram signal, producing a time shifted first electrocardiogram signal; and
combining the time shifted first electrocardiogram signal and the up-sampled baseline variation, producing a second electrocardiogram signal with the baseline variation removed
providing the second electrocardiogram signal by at least one of displaying the second electrocardiogram signal in an electronic visual display, transmitting the second electrocardiogram signal to a remote computing system, storing the second electrocardiogram signal in a physical storage media, or loading the second electrocardiogram signal into memory.

9. The method of claim 8, wherein at least the frequencies above 0.8 hertz are removed from the received first electrocardiogram signal.

10. The method of claim 8, wherein the received first electrocardiogram signal has been sampled at a rate of 500 hertz.

11. The method of claim 8, wherein a polynomial degree of the Savitzky-Golay filter is between 2 and 10.

12. The method of claim 8, wherein a window size of the Savitzky-Golay filter is less than 750.

13. A system comprising:
at least one data processor;
memory storing instructions which, when executed by the at least one data processor, cause the at least one data processor to perform operations comprising:
receiving a first electrocardiogram signal;
processing the first electrocardiogram signal in a filter thereby removing at least high frequency components of the first electrocardiogram signal, producing a filtered first electrocardiogram signal;
down-sampling the filtered first electrocardiogram signal;
processing the down-sampled filtered first electrocardiogram signal in a Savitzky-Golay filter to estimate a baseline variation of the first electrocardiogram signal;
up-sampling the baseline variation;
delaying the first electrocardiogram signal, producing a time shifted first electrocardiogram signal; and
combining the time shifted first electrocardiogram signal and the up-sampled baseline variation, producing a second electrocardiogram signal with the baseline variation removed,
providing the second electrocardiogram signal by at least one of displaying the second electrocardiogram signal in an electronic visual display, transmitting the second electrocardiogram signal to a remote computing system, storing the second electrocardiogram signal in a physical storage media, or loading the second electrocardiogram signal into memory.

14. The system of claim 13, wherein at least the frequencies above 0.8 hertz are removed from the received first electrocardiogram signal.

15. The system of claim 13, wherein the received first electrocardiogram signal has been sampled at a rate of 500 hertz.

16. The system of claim 13, wherein a polynomial degree of the Savitzky-Golay filter is between 2 and 10.

17. The system of claim 13, wherein a window size of the Savitzky-Golay filter is less than 750.

* * * * *